United States Patent [19]

Vanderpool et al.

[11] Patent Number: 4,754,036

[45] Date of Patent: Jun. 28, 1988

[54] CONJOINT PRODUCTION OF C-METHYL TRIETHYLENE DIAMINE AND ALLYL PIPERAZINE

[75] Inventors: Steven H. Vanderpool, New Braunfels; Thomas T. McConnell, Austin, both of Tex.

[73] Assignee: Texaco Inc., White Plains, N.Y.

[21] Appl. No.: 871,940

[22] Filed: Jun. 9, 1986

[51] Int. Cl.$^4$ ................. C07D 487/08; C07D 295/02; C07B 37/10; C07B 35/06
[52] U.S. Cl. ................................. 544/352; 544/351; 544/404
[58] Field of Search ........................ 544/351, 352, 404

[56] References Cited

U.S. PATENT DOCUMENTS

| | | | |
|---|---|---|---|
| 3,285,920 | 11/1966 | Muhlbauer | 544/352 |
| 4,588,842 | 5/1986 | Vanderpool | 564/479 |
| 4,647,664 | 3/1987 | Vanderpool | 544/178 |

Primary Examiner—Mark L. Berch
Attorney, Agent, or Firm—Jack H. Park; Kenneth R. Priem; Carl G. Ries

[57] ABSTRACT

N-(hydroxypropyl) piperazine and/or N,N'-(dihydroxypropyl) piperazine can conjointly be converted to C-methyl-triethylenediamine and allyl piperazine with excellent conjoint yield and selectivity when using a catalyst composed of titania to which from about 0.5 to about 7 wt. % of phosphorus has been thermally chemically bonded in the form of phosphate linkages.

2 Claims, No Drawings

CONJOINT PRODUCTION OF C-METHYL TRIETHYLENE DIAMINE AND ALLYL PIPERAZINE

BACKGROUND OF THE INVENTION

1. Field of the Invention

This invention relates to a catalytic method for the conjoint production of 2-methyl-diazabicyclo-(2.2.2.)-octane(2-methyl-triethylenediamine) and N-allyl piperazine. More particularly, this invention relates to a catalytic method for the conjoint manufacture of 2-methyl-triethylenediamine (MTEDA) and allyl pierazine from N-hydroxypropyl piperazine. Still more particularly, this invention is directed to the use of a catalyst composed of pellets of titania to which a minor amount of phosphorus (0.5 to 7 wt. %) has been thermally chemically bonded in the form of phosphate linkages to catalyze a continuous process for the conjoint manufacture of 2-methyl triethylenediamine and allyl piperazine from N-hydroxypropyl piperazine.

2. Prior Art

The catalysts used in the practice of the process of the present invention are disclosed in Vanderpool U.S. Pat. No. 4,588,842, a division of abandoned Vanderpool U.S. patent application Ser. No. 455,160, filed Jan. 3, 1983, upon which is based European patent application Ser. No. 83,307,520.3 published Aug. 28, 1984, wherein they are disclosed as useful in promoting the reaction of ethylenediamine with ethanolamine to provide essentially linear polyethylenepolyamine reaction products. Minor quantities of cyclic products are also formed.

It has heretofore been proposed to manufacture C-methyl triethylene diamine from a variety of substituted piperazine feedstocks by using appropriate catalysts.

For example, Nieh U.S. Pat. No. 4,092,316 discloses a process for the preparation of C-methyl triethylene diamine (MTEDA) by a liquid phase process wherein a suitable feedstock such as N-(2-hydroxyethyl)-2-methyl piperazine, N-hydroxyethyl)-3-methyl piperazine, N,N'-(di-2-hydroxyethyl)-2-methyl piperazine, N-(hydroxypropyl)piperazine, etc., is heated in the presence of a pentavalent acidic phosphorous compound.

Murakomi et al. U.S. Pat. No. 3,956,329 discloses a process for the dihydrocyclization of nitrogencontaining heterocyclic compounds such as N-hydroxypropyl piperazine to 2-methyltriethylene diamine using a zeolite catalyst.

Czechoslovakian Pat. No. 139,281 to Jezo et al. is directed to the thermal decomposition of 1,4-bis(2-hydroxyalkyl) piperazines in the presence of metal alcoholates such as (MeO)$_2$Mg.

Other procedures are known for the preparation of C-alkyl substituted diazabicyclo-(2,2,2)-octanes by catalytically cyclizing certain substituted piperazine compounds, such as N-hydroxyethyl-methylpiperazines, N,N'-dihydroxyethylmethylpiperazines, etc., in the presence of very specific types of catalysts. Generally, such known procedures are vapor phase reactions which are carried out by contacting the vapors of the substituted piperazine feedstock employed with the acidic-type catalyst at temperatures in excess of about 250° C. to about 500° C. For example, U.S. Pat. No. 3,167,518 to Farkas et al. discloses a method for preparing 2-methyl diazabicyclo-(2,2,2)-octane by cyclodehydrating the reaction product of 2-methylpiperazine with at least an equal molar quantity of ethylene oxide in vapor phase over an active silicious cracking catalyst. More particularly, it is disclosed that the vapor phase cyclodehydration reaction is carried out by passing the ethoxylated 2-methylpiperazine reaction product vapors over a silica-alumina cracking catalyst at a temperature of 325° C. to 425° C.

U.S. Pat. No. 3,297,701 to Brader, Jr. et al. discloses that C-substituted diazabicyclo-(2,2,2)-octanes may be synthesized by the process of contacting a substituted piperazine compound, such as N-aminoethyl-C-alkyl-piperazines, N-hydroxyethyl-C-alkyl-pierazines, etc., in vapor phase with a metal phosphate catalyst in the presence of ammonia at a reaction temperature within the range of 250° C. to about 500° C.

SUMMARY OF INVENTION

It has been surprisingly discovered in accordance with the present invention that N-(hydroxypropyl) piperazine and/or N,N'-(dihydroxypropyl) piperazine may be converted conjointly to MTEDA and allyl piperazine in good yields and excellent selectivities when using a catalyst composed of titania to which from about 0.5 to about 7 wt. % of phosphorus has been thermally chemically bonded in the form of phosphate linkages.

DETAILED DESCRIPTION OF THE EMBODIMENT

Feedstocks

The feedstocks to be used in accordance with the present invention include feedstocks having the formula:

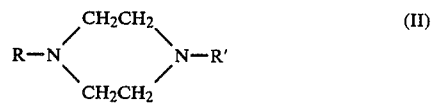 (II)

wherein R represents —CH$_2$CH(CH$_3$)OH and wherein R' represents H.

Reaction Conditions

The reaction of the present invention is conducted utilizing a feedstock of the present invention which is dissolved in water so as to form about a 5 to about 30 wt. % aqueous solution of feedstock, such as a 20 wt. % aqueous solution, which is brought into contact with a catalyst in a batch reactor or in a continuous reactor.

When the reaction is conducted in a batch reactor, the catalyst will preferably be employed in powdered form, whereas when the reaction is conducted on a continuous basis the catalyst is preferably employed in the form of pellets.

The reaction is suitably conducted at a temperature of about 250°–400° C. and, more preferably, at a temperature of about 280° to about 320° C.

The reaction is also preferably conducted at atmospheric pressure. Superatmospheric or subatmospheric pressures may be utilized if desired, but there is no particular advantage in doing so.

When the reaction is conducted on a batch basis, the reaction time may suitably vary from about 0.5 to about 10 hours. When the reaction is conducted on a continuous basis, the feedstock may suitably be passed over a bed of pelleted catalyst at a liquid hourly space velocity (lhsv) of about 0.2 to about 10 volumes of the aqueous solution of the amine feedstock per volume of catalyst per hour. More preferably, the lhsv will be from about 0.5 to about 2.

It is not necessary to use either ammonia or hydrogen as feed components in the practice of the process of the present invention.

Catalysts

The catalyst compositions of the present invention may be used in the form of a fixed bed of catalyst pellets in a continuous reaction system. In a continuous process of this nature, the time of contact of the reactants with the catalyst is one of the interrelated factors that those skilled in the art will adjust, along with temperature, pressure, bed geometry, pellet size, etc. in order to obtain a desired rate of reaction and, hence a desired percentage of conversion of the reactants. In a continuous process, it is not necessary to drive the reaction to completion because unreacted feedstock components can be recycled to the reactor.

It is customary to use cylindrically-shaped catalyst pellets having a diameter essentially equal to the length thereof, such as diameters and lengths ranging from about 0.794 mm (1/32 inch) to about 9.525 mm (⅜ inch). It will be understood that the shape and dimensions of the pellets are not critical to the present invention and that pellets of any suitable shape and dimensions may be used, as desired, by one wishing to practice the process of the present invention.

When cylindrical pellets of catalyst of the type described above are used, the weighted hourly space velocity may be varied within wide limits (e.g., 0.1 to 5 w/hr/w) in order to obtain a desired rate of conversion, as explained above. Normally, space velocities of about 0.5 to 2 w/hr/w will be employed.

The pelleted catalyst compositions of the present invention are advantageously used in a continuous process for the conjoint production of MTEDA and N-allyl piperazine.

The catalyst compositions of the present invention are prepared by depositing a phosphorus compound on titania, as described in greater detail in copending Vanderpool application Ser. No. 06/564,153 filed Dec. 22, 1983, now U.S. Pat. No. 4,588,842, and entitled "Catalytic Preparation of Linear Polyethylenepolyamines" and in said Vanderpool European patent application Ser. No. 83,307,520.3 published Aug. 28, 1984. Pellets of titania may be prepared by extrusion or by compaction in conventional pelleting apparatus using a pelleting aid such as graphite. It is also within the scope of the present invention to deposit the phosphorus compound on powdered titania followed by pelleting and calcination.

Any appropriate water soluble or liquid phosphorus compound can be used as a source of the phosphorus. For convenience, phosphoric acid will normally be used. However, other phosphorus compounds such as phosphoryl chloride ($POCl_3$), phosphorous acid, polyphosphoric acid, phosphorus halides, such as phosphorus bromide, alkyl phosphates and alkyl phosphites such as trimethyl phosphate, triethyl phosphate, trimethyl phosphite, triethyl phosphite, etc. may be utilized. Also, a diamminohydrogen phosphate such as diammonium hydrogen phosphate, $(NH_4)_2HPO_4$, dimethylamino hydrogen phosphate, $(CH_3)_2NH_2PO_4$, diethylaminohydrogen phosphate $(CH_3CH_2)_2NH_2PO_4$, etc. may be used.

As a matter of convenience, the normal practice is to use only one chemical as a phosphorus source (e.g., phosphoric acid). However, mixtures of two or more such reagents may be used if desired.

Preferably the catalyst composition is prepared by impregnating a preformed pellet. A suitable procedure to be used is to heat the water soluble or liquid phosphorus compound at a temperature of about 100° to about 150° C. and to then add pellets in an amount about equal to the volume of the heated liquid. This treatment should be continued from about 0.5 to about 5 hours. At the end of that time, the resulting mixture of pellets and liquid is cooled, decanted to remove excess liquid followed by washing with an amount of water adequate to substantially completely remove unadsorbed liquid. Temperatures above 150° C. can be used, if desired, but there is no particular advantage in doing so.

It will be understood that the phosphorus that is present on a thus-treated pellet is not present as elemental phosphorus, but rather as phosphorus that is chemically bound, as an oxide, to the titania. This is demonstrated by the fact that repeated washing will not remove all of the phosphorus. However, the exact nature of the bonding is not completely understood.

The amount of phosphorus that is bonded to the support is a function of heating and other conditions used in the treating step and is also a function of the chemical identity of the phosphorus compound that is used as a source of phosphorus. Under the treating conditions exemplified above, at least about 0.5 wt % of phosphorus is caused to bond (i.e., permanently adhere) to the pellets. There is an upper limit to the amount of phosphorus that bonds to the support. This upper limit is, as indicated, a function of both the treating conditions and the chemical used as a source of the phosphorus. Normally, the maximum amount of phosphorus that can be caused to bond to the pellets is about 7 wt. %.

When the pellets are impregnated with the phosphorus compound at a temperature of at least about 100° C., there is no absolute need to calcine the catalyst composition before use. However, the pellets can be calcined prior to use, if desired, as a precautionary measure and/or in order to still further improve the physical properties of the pellets. The pellets are suitably calcined at a temperature of about 200° C. to about 800° C. for a period of time within the range of 2 to 24 hours; more preferably at a temperature of about 300° C. to about 600° C. for about 4 to 16 hours.

Other procedures can be used in adding phosphorus to the titania. For example, the pellets can be treated with the phosphorus compound at ambient temperatures or at more modest elevated temperatures of less than about 100° C.

Alternatively, the titania can be treated with the phosphorus-containing compound in powdered form and the powder can thereafter be pelleted, if desired. If the treatment is conducted at a temperature of about 100° C. or more, thermal activation will normally have been obtained and it will not be absolutely necessary to perform a calcining operation prior to use. If lower treating temperatures are used, calcining is normally a desired operation. The calcining operation can be conducted prior to or subsequent to the pelleting step. Any appropriate pelleting procedure of the type known to those skilled in the art may be used. For example, the treated powdered titania can be mixed with graphite and/or other binders and compacted or extruded under conventional conditions.

In any event, in-situ calcining will occur when the pelleted catalyst composition is used to catalyze the conversion of N-(hydroxypropyl) piperazine to MTEDA and N-(allyl) piperazine at 300° to 400° C., as hereinafter more fully set forth.

Products

The product of the present invention, 2-methyl triethylene diamine (MTEDA), is a compound having the formula:

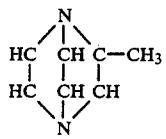

(I)

The conjoint reaction product is N-(allyl) piperazine having the formula:

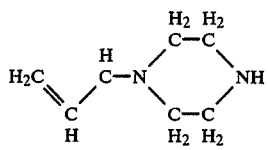

EXAMPLE

Equipment and Procedures

The example was performed in a 100 cc reactor constructed of ¾ inch stainless steel tubing connected to ⅛ inch feed and effluent lines with swagelok fittings. The reactor tube was situated inside of a 3×3 inch aluminum block which was heated electrically with four 1000 watt strip heaters. Temperature control was achieved with a Thermoelectric controller monitoring thermocouples attached to the skin of the reactor body. The feed was charged to the reactor system with a Beckman 110A L.C. pump. For safety, pressure relief was provided by a 3000 lb. rupture disk assembly although all runs were preformed at atmospheric pressure to minimize bimolecular reactions. The reactor effluent was collected in a glass jug and sampled after the system had lined-out at the proscribed temperature for at least 2.5 hours.

In general the feedstock consisted of a 4:1 aqueous feed, consisted of 4 parts water by weight and 1 part N-(hydroxypropyl) piperazine by weight.

Analysis of the reactor effluent was achieved using an OV-17 column in a Hewlett-Packard 5710A gas chromatograph. Analysis was on a water-free and feedfree basis. Snce the conversion of N-(hydroxypropyl) piperazine was nearly quantitative, the selectivities were close to calculated yields.

The tubular reactor with about 100 cc of a pelleted titania-phosphorus catalyst containing about 2 wt. % of phosphorus prepared by dipping the preformed titania pellets into a 30% polyphosphoric acid solution, followed by decanting and calcining at 450° C.

The feed was prepared by propoxylating piperazine in methanol solution at about 90° C. The methanol was then removed by vacuum distillation. This PO/PIP adduct was then diluted to make a 20% solution by weight for use as reactor feed.

At 300° C., conversion of the PO/PIP adduct was >99%. The major product was Allylpiperazine, selectivity 34% and MTEDA, selectivity 24%. Selectivity data is approximate area % on a water-free analysis of crude reactor effluent. Allylpiperazine was identified by GC/IR.

The foregoing examples are given by way of illustration and are not intended as limitations on the scope of this invention, as defined by the appended claims.

What is claimed is:

1. A method for the conjoint manufacture of C-methyl-triethylenediamine and N-allyl piperazine which comprises bringing an aqueous solution of N-2-hydroxy-n-propyl piperazine containing about 5 to about 30 wt. % of said N-2-hydroxy-n-propyl piperazine into contact with a cyclization catalyst at a temperature of about 250°–400° C. for a period of time sufficient to conjointly convert at least a portion of said N-2-hydroxy-n-propyl piperazine to C-methyl-triethylenediamine and N-allyl piperazine;

said catalyst composition consisting essentially of titania having from about 0.5 to about 7 wt. % of phosphorus thermally chemically bonded to the surface thereof in the form of phosphate bonds.

2. A method for the conjoint manufacture of C-methyl-triethylenediamine and N-allyl piperazine which comprises forming an aqueous solution of N-2-hydroxy-n-propyl piperazine containing about 5 to about 30 wt. % of said N-2-hydroxy-n-propyl piperazine, continuously bringing said aqueous solution into contact with a pelleted cyclization catalyst at a temperature of about 250° to about 400° C. at a liquid hourly space velocity of about 0.2 to about 10 sufficient to convert said N-2-hydroxy-n-propyl piperazine into a reaction product predominantly containing C-methyl-triethylenediamine and N-allyl piperazine, continuously recovering an aqueous solution of said reaction product and continuously distilling said reaction product to obtain C-methyl-triethylenediamine and allyl piperazine, said catalyst composition consisting essentially of titania having from about 0.5 to about 7 wt. % of phosphorus thermally chemically bonded to the surface thereof in the form of phosphate bonds.

* * * * *